United States Patent [19]

Kaeding et al.

[11] 4,094,921

[45] June 13, 1978

[54] SELECTIVE ETHYLATION OF MONO ALKYL BENZENES

[75] Inventors: Warren W. Kaeding, Westfield; Lewis B. Young, Kendall Park, both of N.J.

[73] Assignee: Mobil Oil Corporation, New York, N.Y.

[21] Appl. No.: 787,716

[22] Filed: Apr. 15, 1977

Related U.S. Application Data

[63] Continuation-in-part of Ser. No. 706,981, Jul. 19, 1976.

[51] Int. Cl.[2] .......................... C07C 3/52; C07C 15/10

[52] U.S. Cl. ............................ 260/671 C; 260/669 R; 260/671 R

[58] Field of Search ............ 260/671 R, 671 C, 669 R

[56] References Cited

U.S. PATENT DOCUMENTS

| | | | |
|---|---|---|---|
| 3,299,155 | 1/1967 | Adams | 260/669 R |
| 3,525,776 | 8/1970 | Berger | 260/669 R |
| 3,751,506 | 8/1973 | Burress | 260/671 C |
| 3,965,207 | 6/1976 | Weinstein | 260/671 C |
| 3,965,209 | 6/1976 | Butter et al. | 260/671 C |
| 4,001,346 | 1/1977 | Chu | 260/671 C |
| 4,002,697 | 1/1977 | Chen | 260/671 C |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

A catalytic process is provided for the ethylation of a mono alkyl benzene wherein the alkyl substituent contains 1 or 2 carbon atoms, i.e. toluene or ethylbenzene, to selectively produce the para and meta derivatives of said mono alkyl benzene to the exclusion or substantial exclusion of the ortho derivative thereof by contacting said mono alkyl benzene, under conversion conditions, with an ethylating agent in the presence of a catalyst comprising a crystalline aluminosilicate zeolite, which zeolite is characterized by an activity, in terms of alpha value, of between about 2 and about 5000, and preferably between about 20 and about 500, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, said crystalline aluminosilicate zeolite being further characterized by having a silica to alumina ratio of at least about 12 and a constraint index, as hereinafter defined, within the approximate range of 1 to 12, said catalyst having been subjected to steam treatment at a temperature between about 250 and about 1000° C. for a period of between about 0.5 and about 100 hours.

20 Claims, No Drawings

SELECTIVE ETHYLATION OF MONO ALKYL BENZENES

CROSS REFERENCE TO RELATED APPLICATIONS

This application is a continuation-in-part of co-pending application Ser. No. 706,981 filed July 19, 1976.

BACKGROUND OF THE INVENTION

1. Field of the Invention

This invention relates to a process for selectively converting toluene or ethylbenzene to the para and meta ethyl derivatives thereof, utilizing a specified steam treated crystalline aluminosilicate zeolite catalyst.

2. Description of the Prior Art

Alkylation of aromatic hydrocarbons utilizing crystalline aluminosilicate catalysts has heretofore been described. U.S. Pat. No. 2,904,697 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation of aromatic hydrocarbons in the presence of X- or Y-type crystalline aluminosilicate zeolites, specifically such type zeolites wherein the cation is rare earth and/or hydrogen. U.S. Pat. Nos. 3,751,504 to Keown et al. and 3,751,506 to Burress describe vapor phase alkylation of aromatic hydrocarbons with olefins, e.g. benzene with ethylene, in the presence of a ZSM-5 type zeolite catalyst.

While the above-noted prior art is considered of interest in connection with the subject matter of the present invention, the selective ethylation process described herein utilizing a catalyst of a crystalline aluminosilicate zeolite, said zeolite having a silica/alumina ratio of at least about 12 and a constraint index of 1 to 12, which catalyst has undergone prior modification by treatment with steam to alter the activity and sorption characteristics thereof to achieve unexpectedly high selective production of the para and meta derivatives of a mono alkyl benzene, substantially free of ortho derivative thereof has not, insofar as is known, been heretofore described.

Both ethyltoluene and diethylbenzene are valuable chemicals. Thus, ethyltoluene may further be dehydrogenated to produce the corresponding vinyltoluene. The latter is used, to a large extent, in fiberglass-reinforced polyesters where the lower volatility of vinyltoluene and the reduced shrinkage in the final product make it superior over corresponding use of styrene. Vinyltoluene is also used to a lesser extent in alkyd paints where it has the advantage over styrene of a higher flash point and better film toughness. Copolymers of vinyltoluene with butadiene and with alpha-methylstyrene are used in adhesives, traffic paints, inks and hot melts where their principal advantage is rapid dry or cure time.

It has heretofore been recognized that the presence of substantial quantities of the ortho isomers is highly undesirable in the charge undergoing dehydrogenation since it tends to lead to ring closure with formation of the corresponding indenes and indanes which adversely affect the properties of the resultant polymer. The indenes and indanes so formed are difficult to separate from the desired vinyl aromatic products. It has accordingly heretofore been necessary to remove the ortho isomers from the ethyltoluene and diethylbenzene charge stocks by expensive distillation techniques prior to dehydrogenation thereof.

It is evident that the availability of ethyltoluene or diethylbenzene in which the ortho isomer is initially absent or present only in trace amount would eliminate the necessity for expensive prior removal of this isomer. Such products have, however, not heretofore been available.

SUMMARY OF THE INVENTION

In accordance with the present invention, a process has been discovered for producing ethyltoluene or diethylbenzene virtually free from the undesired ortho isomer, thus eliminating the heretofore necessary expensive purification procedure. Following the teachings of this invention, para-ethyltoluene and meta-ethyltoluene or para-diethylbenzene and meta-diethylbenzene are produced in admixture, together with at best only trace amounts of the corresponding ortho isomer.

The process of the invention involves ethylation of a mono alkyl benzene wherein the alkyl substituent contains 1 or 2 carbon atoms by contacting said mono alkyl benzene with an ethylating agent, under conversion conditions, in the presence of a catalyst having a controlled hexane crackling activity, a minimum diffusion time for ortho-xylene and a minimum xylene sorption capacity. More particularly, the zeolite utilized herein is characterized by an activity, in terms of alpha value, of between about 2 and about 5000, a xylene sorption capacity greater than 1 gram/100 grams of zeolite and an ortho xylene sorption time for 30 percent of said capacity of greater than 10 minutes, where the sorption capacity and sorption time are measured at 120° C. and a xylene pressure of 4.5 $\pm$ 0.8 mm. of mercury. The catalyst, prior to use, is steamed at a temperature between about 250 and about 1000° C. for a period of between about 0.5 and about 100 hours and preferably at a temperature between about 400° and about 700° C. for a period of between about 1 and about 24 hours.

In a preferred embodiment the present process comprises ethylation of toluene or ethylbenzene to yield ethyltoluene or diethylbenzene in which the proportion of either or both of the para and meta isomers are substantially in excess of their normal equilibrium concentration and the proportion of the ortho isomer is very substantially less than its normal equilibrium concentration and desirably present only in trace or lesser amount. The process of the present invention has the advantage and flexibility of providing a wide range of mixed para and meta ethyltoluene or mixed para and meta diethylbenzene. Thus, the ratio of para/meta isomer produced may be varied from about 30/70 to about 70/30 depending on the conditions and extent of steam treatment as well as on the crystal size of the crystalline aluminosilicate zeolite employed.

Ethylation is effectively accomplished at a temperature between about 250° and about 600° C. at a pressure of between about 0.1 and about 100 atmospheres utilizing a feed weight hourly space velocity (WHSV) between about 0.1 and about 100. The latter WHSV is based upon the weight of catalyst composition, i.e. total weight of active catalyst and binder therefor. The molar feed ratio of mono alkyl benzene/ethylating agent is generally between about 1 and about 10.

DESCRIPTION OF SPECIFIC EMBODIMENTS

The mono alkyl benzene undergoing ethylation in accordance with this invention is one wherein the alkyl substituent is methyl or ethyl, i.e. toluene or ethylbenzene. The ethylating agent is generally ethylene or a gaseous mixture high in this reactant, including petroleum refinery streams or other feasible product sources. Other suitable ethylating agents include ethyl alcohol and ethyl halides, e.g. ethyl chloride; diethyl ether, diethyl sulfide and ethylmercaptan.

In accordance with the present invention, the above described reactants are brought into contact, under conversion conditions, with a bed comprising particle-form catalyst containing a crystalline aluminosilicate having: (1) an activity, in terms of alpha value, of between about 2 and about 5000, (2) a xylene sorption capacity greater than 1 gram/100 grams of zeolite and (3) an ortho-xylene sorption time for 30 percent of said capacity of greater than 10 minutes, where the sorption capacity and sorption time are measured at 120° C. and a xylene pressure of 4.5 ± 0.8 mm. of mercury.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per unit volume of zeolite and compared with that of silica-alumina catalyst which is normalized to a reference activity of 1000° F. Catalytic activity of the catalysts are expressed as multiple of this standard, i.e. the silica-alumina standard. The silica-alumina reference catalyst contains about 10 weight percent $Al_2O_3$ and remainder $SiO_2$. This method of determining alpha, modified as described above, is more fully described in the Journal of Catalysis, Vol. VI, Pages 278–287, 1966.

The measurements of hydrocarbon sorption capacities and rates are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time of at least 1 gram per 100 grams of zeolite measured at 120° C. and a xylene pressure of 4.5 ± 0.8 mm. of mercury and an orthoxylene sorption time for 30 percent of said capacity of greater than 10 minutes (at the same conditions of temperature and pressure) are required in order to achieve the desired selective production of para and meta diethyltoluenes.

It has been found that zeolites exhibiting the desired selectivity require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

$$t_{0.3} = F.t_{0.05}$$

| Percent of sorption capacity | Factor(F) to Estimate 30% Sorption time |
|---|---|
| 5 | 36 |
| 10 | 9 |
| 20 | 2.2 |

The zeolite catalysts utilized herein are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram of less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passsed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{ (fraction of n-hexane remaining)}}{\log_{10} \text{ (fraction of 3-methylpentane remaining)}}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3\text{–}2.5)R_2O : (0\text{–}0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4\text{–}2.5)R_2O : (0\text{–}0.6)M_2O : Al_2O_3 : xSiO_2$$

wherein R is an organic nitrogen-containing cation derived from a 2-hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.38A.

TABLE I

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| $R^+ + M^+$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 |

wherein R is an organic nitrogen-containing cation derived from a 2-(hydroxyalkyl) trialkylammonium compound and M is an alkali metal ion, and maintaining the mixture until crystals of the zeolite are formed. (The quantity of OH— is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such a range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

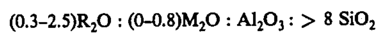

$$(0.3\text{–}2.5)R_2O : (0\text{–}0.8)M_2O : Al_2O_3 : > 8\ SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

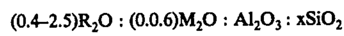

$$(0.4\text{–}2.5)R_2O : (0.0.6)M_2O : Al_2O_3 : xSiO_2$$

wherein R is an organic nitrogen-containing cation derived from ethylenediamine or pyrrolidine, M is an alkali metal, especially sodium, and $x$ is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d (A) | I/Io |
|---|---|
| 9.6 ± 0.2 – | Very Strong-Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| $R^+ + M^+$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 |

wherein R is an organic nitrogen-containing cation derived from pyrrolidone or ethylenediamine and M is an alkali metal ion, and maintaining the mixture until crystals of the zeolite are formed. (The quantity of OH— is calculated only from the inorganic sources of alkali without any organic base contribution). Thereafter, the crystals are separated from the liquid and recovered. Typical reaction conditions consist of heating the foregoing reaction mixture to a temperature of from about 90° to about 400° C. for a period of time of from about 6 hours to about 100 days. A more preferred temperature range is from about 150° to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because the tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

It is also feasible to dilute or physically mix particles of the above-described crystalline aluminosilicate zeolites with particles of material substantially devoid of catalytic activity, such as, for example, low surface area quartz or with particles having appropriate catalytic activity and which may be either amorphous or crystalline.

The crystalline aluminosilicate zeolite catalysts employed are, in accordance with the present invention, treated prior to use with an atmosphere containing from about 5 to about 100 percent steam at a temperature of from about 250 to about 1000° C. for a period of between about 0.5 and about 100 hours and preferably at a temperature between about 400° C. and about 700° C. for a period of between about 1 and about 24 hours and under pressures ranging from sub-atmospheric to several hundred atmospheres to reduce the alpha value thereof, where the initial alpha value was greater than 500, to less than 500 and preferably less than 20 but greater than zero.

It is also within the purview of this invention that the hereindescribed zeolite catalyst may, in some instances, desirably undergo precoking prior to the specified steam treatment. Precoking can be accomplished by contacting the catalyst with a hydrocarbon charge, e.g. toluene, under high severity conditions for a sufficient time to deposit the desired amount of coke thereon. Generally, between about 2 and about 75 and preferably between about 15 and about 75 weight percent of coke is deposited on the catalyst when the precoking technique is employed.

It has further been found that the crystal size of the crystalline aluminosilicate zeolite employed is a factor influencing the desired selective production of para and meta ethyltoluene or diethylbenzene with suppression of the formation of the ortho isomer. While microcrystalline zeolites of the type described hereinabove having a crystal size in the approximate range of 0.01 to 0.10 micron may be employed, it is a preferred embodiment of the invention to utilize crystalline aluminosilicate zeolites of a crystal size greater than about 1 micron and generally in the approximate range of 1 to 40 microns. Particularly preferred are those zeolites having crystal sizes within the approximate range of 1 to 6 microns since it has been established that with the use of such size crystals, steam treated, as described hereinabove, the production of the undesired ortho isomer is eliminated.

In one preferred embodiment of the present invention, the para and meta ethyltoluene or diethylbenzene mixture produced, free of the ortho isomer, is conducted directly to a dehydrogenation zone, without requiring an intermediate distillation or other separation treatment to remove the ortho isomer, where the charge is dehydrogenated to yield desired vinyltoluene or divinylbenzene. It is contemplated that dehydrogenation will be carried out under conventional dehydrogenation conditions including a temperature between about 400° and about 800° C. and preferably between about 500° and about 700° C. and a pressure between about 5 and about 100 psig. Dehydrogenation may be effected in nitrogen, an oxygen-containing gas and/or steam atmosphere, preferably atmospheric. Suitable dehydrogenation catalysts include oxides of nickel, chromium, molybdenum, iron, and zinc, optionally mixed with smaller amounts of basic oxides such as oxides of lithium, sodium or potassium. Particularly preferred are catalytic compositions comprising oxides of iron, potassium and chromium, such as 70–80% $Fe_2O_3$, 20–25% $K_2O$ and 1–5% $Cr_2O_3$.

The conversion process described herein may be carried out as a batch type, semi-continuous or continuous operation utilizing a fixed or moving bed catalyst system. The catalyst after use in a moving bed reactor is conducted to a regeneration zone wherein coke is burned from the catalyst in an oxygen-containing atmosphere, e.g. air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5–2%) is used to burn the coke in a controlled manner so as to limit the temperature to a maximum of around 500°–550° C.

The following examples will serve to illustrate the process of this invention without limiting the same:

EXAMPLE 1

Five grams, 9.6 cc, of HZSM-5 having a crystallite size of 0.02 to 0.05 microns, were pressed into wafers, crushed and sized to 14–20 mesh size particles. These particles were uniformly diluted with 4 volumes of low surface area quartz of the same size and tested for ability to alkylate toluene with ethylene to yield ethyltoluene. Since the limiting reactant was ethylene, the maximum theoretical conversion of toluene was about 25 percent. The conditions of reaction and results are shown in Table I below.

TABLE I

| | | WHSV | | | | CONVERSION | | SELECTIVITY | | | ETHYLTOLUENE ISOMER | | |
|---|---|---|---|---|---|---|---|---|---|---|---|---|---|
| Run No. | Temp ° C. | Toluene | Ethylene | Hours On Stream | Steaming Catalyst[a] Hours | Toluene % | Ethylene % | Ethyl-Toluene % | Other Aromatics % | Light Gas % | Para % | Meta % | Ortho % |
| 1 | 350 | 6.9 | .5 | 1 | 0 | 20.4 | 92.6 | 88.7 | 10.7 | .6 | 26.8 | 60.6 | 12.6 |
| 2 | 350 | 6.9 | .5 | 19.5 | 0 | 19.4 | 95.9 | 89.1 | 9.5 | 1.4 | 27.1 | 61.8 | 10.1 |
| [b] 3 | 400 | 6.9 | .5 | 49 | 0 | 20.3 | 91.2 | 84.2 | 14.3 | 1.5 | 26.4 | 58.9 | 14.7 |
| [b] 4 | 350 | 6.9 | .5 | 90 | 0 | 19.7 | 88.1 | 81.4 | 16.5 | 2.1 | 26.9 | 59.3 | 13.8 |
| [b] 5 | 350 | 6.9 | .5 | 97 | 1 | 24.8 | 78.1 | 94.8 | 4.0 | 1.2 | 35.9 | 63.2 | .9 |
| 6 | 350 | 6.9 | .5 | 98 | 2 | 23.0 | 67.5 | 95.7 | 3.5 | .8 | 37.3 | 61.8 | .9 |
| [b] 7 | 350 | 6.9 | .5 | 99 | 4 | 18.3 | 68.8 | 96.4 | 2.9 | .7 | 38.8 | 60.5 | .7 |
| [b] 8 | 350 | 7.0 | .5 | 100 | 6 | 11.1 | 74.6 | 99.1 | .5 | .4 | 40.7 | 59.3 | 0 |
| 9 | 350 | 7.0 | .5 | 118 | 6 | 11.5 | 52.6 | 99.2 | .5 | .3 | 42.6 | 57.4 | 0 |
| [b] 10 | 400 | 7.0 | .5 | 119 | 6 | 17.6 | 68.5 | 99.0 | .8 | .2 | 35.1 | 63.0 | 1.9 |
| 11 | 400 | 7.0 | .5 | 139 | 6 | 18.0 | 75.1 | 99.3 | .5 | .2 | 36.2 | 62.7 | 1.1 |

[a] Temp 600° C., 19.8 grams liq. water/hr for 5 grams of catalyst

[b] Catalyst calcined in air at 550° C. for 2-16 hrs. to remove any residual coke Each of the above tabulated runs represents the collected gas and liquid product sample for a period of one hour. It will be evident from the first four runs that the toluene conversion was about 20 percent (80% of theory), that all three ethyltoluene isomers were formed and that the selectivity to ethyltoluenes was between about 80 and 90 percent.

Prior to Run 5, the catalyst was treated with steam, at a temperature of 600° C., for one hour, at a feed rate of liquid water of about 20 ml. per hour. The results after steaming the catalyst for one hour are shown by Run 5, from which it is seen that the amount of ortho isomer was very substantially reduced and that the amount of para isomer was increased. In addition, the selectivity to the desired ethyltoluene product was increased significantly to about 95 percent at the expense of undesired side reaction products. The latter include other aromatics, such as benzene, toluene, xylenes and diethylbenzene and light gases such as ethane, propane, propylene and $C_4$ olefins and paraffins. In a similar manner, the catalyst was steamed for a second hour to give a total of two hours. The results of using this catalyst are shown in Run 6. The results of further steaming up to a total of six hours are shown in the subsequent runs.

Runs 8 and 9 show the results of the first and last hour samples for 18 hour runs. It is evident that at 350° C. after 6 hours of steaming that no detectable amount of ortho isomer was produced. Furthermore, the selectivity to the desired meta/para ethyltoluene mixture was 99 percent of the theoretical yield.

EXAMPLE 2

In a manner similar to Example 1, 3.25 grams of HZSM-5 having a crystallite size of 0.02 to 0.05 micron was used. In this example, the HZSM-5 sample was mixed with 1.75 grams of alumina binder and extruded to produce a 1/16 inch cylindrical particle. The extrudate with a volume of 9 ml. was diluted with 4 volumes of low surface area quartz and tested for ability to alkylate toluene with ethylene to yield ethyltoluene. The conditions of reaction and results are shown in Table II below.

TABLE II

| | | WHSV | | | | CONVERSION | | SELECTIVITY | | | ETHYLTOLUENE ISOMER | | |
|---|---|---|---|---|---|---|---|---|---|---|---|---|---|
| Run No. | Temp ° C. | Toluene | Ethylene | Hours On Stream | Steaming Catalyst[(a)] Hours | Toluene % | Ethylene % | Ethyl-Toluene % | Other Aromatics % | Light Gas % | Para % | Meta % | Ortho % |
| 1 | 350 | 6.9 | .5 | 1 | 0 | 21.7 | 95.2 | 87.7 | 9.6 | 2.7 | 29.4 | 61.4 | 9.2 |
| 2 b | 350 | 6.9 | .5 | 20 | 0 | 22.8 | 94.5 | 87.4 | 10.1 | 2.5 | 30.7 | 62.4 | 6.9 |
| 3 | 400 | 6.9 | .5 | 21 | 0 | 22.5 | 90.5 | 76.4 | 19.0 | 4.6 | 28.2 | 58.6 | 13.2 |
| 4 b | 400 | 6.9 | .5 | 40 | 0 | 21.6 | 90.5 | 84.0 | 13.6 | 2.4 | 28.8 | 59.6 | 11.6 |
| 5 | 350 | 6.9 | .5 | 41 | 1 | 18.4 | 85.6 | 95.8 | 3.5 | .7 | 35.5 | 62.6 | 1.8 |
| 6 b | 350 | 6.9 | .5 | 59 | 1 | 17.0 | 77.3 | 96.2 | 2.4 | .4 | 38.1 | 60.9 | 1.0 |
| 7 | 350 | 6.9 | .5 | 60 | 2 | 19.2 | 74.5 | 95.6 | 3.4 | 1.0 | 37.4 | 61.3 | 1.3 |
| 8 b | 350 | 6.9 | .5 | 62 | 2 | 18.7 | 75.0 | 95.0 | 3.0 | 2.0 | 37.9 | 60.9 | 1.1 |
| 9 | 350 | 6.9 | .5 | 63 | 3 | 17.1 | 63.7 | 95.2 | 3.5 | 1.3 | 39.7 | 59.4 | 1.0 |
| 10 b | 350 | 6.9 | .5 | 65 | 3 | 16.5 | 61.1 | 96.2 | 3.1 | .7 | 40.3 | 58.9 | .8 |
| 11 | 350 | 6.9 | .5 | 66 | 4 | 15.2 | 60.8 | 95.3 | 3.4 | 1.3 | 40.8 | 58.4 | .8 |
| 12 | 350 | 6.9 | .5 | 68 | 4 | 15.1 | 60.1 | 96.6 | 2.8 | .6 | 40.4 | 58.8 | .8 |

[(a)] Temp 600° C., 19.8 grams liq. water/hr for 5 grams of catalyst
[(b)] Catalyst calcined in air at 550° C. for 2-16 hrs. to remove any residual coke The first four runs in the above table show the results with unsteamed catalysts at 350° and 400° C. The results for the first and last hour of a 20 hour operation for each temperature are shown. Subsequent runs show the results of successive one hour steaming periods at 600° C. up to a total of four hours. The results obtained are, in general, similar to those described in Example 1 and set forth in Table I.

EXAMPLE 3

In a manner similar to the preceding examples, 3.25 grams of HZSM-5 but having a crystallite size of about 2 microns was mixed with 1.75 grams of alumina binder and extruded to produce a 1/16 inch cylindrical particle. The extrudate with a volume of 8.5 ml. was diluted with 4 volumes of low surface area quartz and tested for its ability to alkylate toluene with ethylene to yield ethyltoluene. The conditions of reaction and results are shown in Table III below.

TABLE III

| | | WHSV | | | | CONVERSION | | SELECTIVITY | | | ETHYLTOLUENE ISOMER | | |
|---|---|---|---|---|---|---|---|---|---|---|---|---|---|
| Run No. | Temp ° C. | Toluene | Ethylene | Hours On Stream | Steaming Catalyst[(a)] Hours | Toluene % | Ethylene % | Ethyl-Toluene % | Other Aromatics % | Light Gas % | Para % | Meta % | Ortho % |
| 1 | 350 | 6.9 | .5 | 1 | 0 | 20.5 | 97.2 | 84.5 | 11.1 | 4.4 | 36.9 | 61.6 | 1.6 |
| 2 b | 350 | 6.9 | .5 | 19 | 0 | 22.6 | 75.0 | 92.3 | 5.7 | 2.0 | 58.0 | 41.3 | .7 |
| 3 | 400 | 6.9 | .5 | 20 | 0 | 20.4 | 90.1 | 80.2 | 16.2 | 3.6 | 31.3 | 64.8 | 3.8 |
| 4 b | 400 | 6.9 | .5 | 38 | 0 | 19.2 | 89.2 | 87.2 | 10.8 | 2.0 | 33.5 | 63.9 | 2.7 |
| 5 | 350 | 6.9 | .5 | 39 | 1 | 18.1 | 91.5 | 89.3 | 8.3 | 2.4 | 51.3 | 48.4 | .3 |
| 6 b | 350 | 6.9 | .5 | 57 | 1 | 20.2 | 79.5 | 94.4 | 4.6 | 1.0 | 60.8 | 39.2 | 0 |
| 7 | 350 | 6.9 | .5 | 58 | 2 | 17.4 | 86.4 | 91.6 | 6.3 | 2.1 | 58.9 | 41.1 | 0 |
| 8 b | 350 | 6.9 | .5 | 60 | 2 | 18.1 | 81.5 | 94.6 | 5.1 | .3 | 58.1 | 41.9 | 0 |
| 9 | 350 | 6.9 | .5 | 61 | 3 | 17.0 | 80.8 | 93.0 | 5.1 | 1.9 | 64.0 | 36.0 | 0 |
| 10 b | 350 | 6.9 | .5 | 63 | 3 | 16.1 | 76.7 | 94.5 | 4.4 | 1.1 | 65.7 | 34.3 | 0 |

TABLE III-continued

| Run No. | Temp ° C. | WHSV Toluene | WHSV Ethylene | Hours On Stream | Steaming Catalyst[a] Hours | CONVERSION Toluene % | CONVERSION Ethylene % | SELECTIVITY Ethyl-Toluene % | SELECTIVITY Other Aromatics % | SELECTIVITY Light Gas % | ETHYLTOLUENE ISOMER Para % | ETHYLTOLUENE ISOMER Meta % | ETHYLTOLUENE ISOMER Ortho % |
|---|---|---|---|---|---|---|---|---|---|---|---|---|---|
| 11 | 350 | 6.9 | .5 | 64 | 4 | 15.8 | 74.1 | 93.1 | 5.2 | 1.7 | 67.2 | 32.8 | 0 |
| 12 | 350 | 6.9 | .5 | 66 | 4 | 15.1 | 71.4 | 94.5 | 4.5 | 1.0 | 67.9 | 32.1 | 0 |

[a] Temp 600° C., 19.8 grams liq. water/hr for 5 grams of catalyst
[b] Catalyst calcined in air at 550° C. for 2–16 hrs. to remove any residual coke Comparing the runs made with steamed and unsteamed catalysts, it will be seen that steaming reduced the amount of ortho ethyltoluene to a value below the level of detection. In addition, the ratio of remaining para/meta isomers was increased significantly over comparable results obtained using the microcrystalline zeolite of 0.02 to 0.05 micron size employed in Examples 1 and 2. It is accordingly evident that various mixtures of para and meta ethyltoluene, free from the undesired ortho isomer, can be obtained with variation in zeolite crystal size, the content of para isomer increasing with the use of larger crystalline size zeolite.

EXAMPLE 4

Toluene was alkylated with ethylene in the presence of a catalyst of HZSM-5 having a crystallite size of 0.02 to 0.05 micron. The conditions of reaction and analytical results are summarized in Table IV below.

TAVLE IV

| Run No. | 1 | 2 | 3 | 4 |
|---|---|---|---|---|
| Temp ° C | 300 | 350 | 350 | 350 |
| WHSV | 7.4 | 7.4 | 3.9 | 10.9 |
| Molar Feed Ratio Toluene/Ethylene | 5 | 5 | 2.5 | 7.6 |
| Stream Time, Hrs. | 1 | 2 | 3 | 4 |
| Conversion Wt. % Toluene | 15.6 | 18.5 | 36.2 | 13.0 |
| Conversion Wt. % Ethylene | 89.0 | 91.4 | 86.7 | 90.5 |
| Ethyl Toluene Para | 31.95 | 28.96 | 28.54 | 29.61 |
| Meta | 61.40 | 56.83 | 56.56 | 58.07 |
| Ortho | 6.65 | 14.21 | 14.90 | 12.32 |

It is evident from the above results that the HZSM-5 catalyst, which had not undergone steam treatment as described hereinabove, was non-selective for the desired production of para and meta ethyltoluene. Equilibrium concentration of ethyltoluene is 31.5 percent para, 50.2 percent meta and 18.3 percent ortho. In the above runs, all three isomers were produced in amounts not substantially different from the thermodynamic equilibrium illustrating that the above-described steam treatment is necessary in achieving desired selective production of the para and meta isomers.

EXAMPLE 5

Toluene was alkylated with ethylene in the presence of a catalyst of HZSM-5 having a crystallite size of about 2 microns. The conditions of reaction and analytical results are summarized in Table V below.

TABLE V

| Run No. | 1 | 2 |
|---|---|---|
| Temp ° C | 300 | 400 |
| WHSV | 3.8 | 3.8 |
| Molar Feed Ratio Toluene/Ethylene | 2.1 | 2.1 |
| Stream Time, Hrs. | 3 | 4 |
| Conversion Wt. % Toluene | 4.4 | 22.7 |
| Conversion Wt. % Ethylene | 18.6 | 79.2 |
| Ethyl Toluene Para | 58.1 | 33.0 |
| Meta | 39.9 | 65.4 |
| Ortho | 2.0 | 1.6 |

It will be seen from the above results that the ratio of para to meta isomer changed considerably with temperature. It is also evident that while the amount of the ortho isomer was reduced considerably from the equilibrium amount of 18.3 percent, the elimination of this undesired isomer from the reaction product mixture was not achieved as was realized with use of the steamed catalyst employed in the process described herein.

EXAMPLE 6

A 5.3 gram sample of HZSM-5 having a crystallite size of about 2 micron was steamed at 515° C. for a period of 2 hours and a feed rate of 8.8 cc of liquid water per hour. The temperature was then raised to 640° C. Toluene was then fed at a rate of 180 ml per hour for a period of 4 hours and 15 minutes. The temperature was then reduced to 550° C., the catalyst flushed with nitrogen and then cooled to yield a coke-containing product.

EXAMPLE 7

Toluene was alkylated with ethylene in the presence of the catalyst of Example 6. The conditions of reaction and analytical results are summarized in Table VI below.

TABLE VI

| Run No. | 1 | 2 | 3 | 4 |
|---|---|---|---|---|
| Temp ° C | 300 | 350 | 350 | 350 |
| WHSV | 7.4 | 7.4 | 4.0 | 7.4 |
| Molar Feed Ratio Toluene/Ethylene | 5 | 5 | 2.5 | 5 |
| Stream Time, Hrs. | 1 | 2 | 3 | 4 |
| Conversion Wt. % Toluene | 4.1 | 16.8 | 25.9 | 14.4 |
| Conversion Wt. % Ethylene | 24.1 | 76.8 | 67.6 | 65.6 |
| Ethyl Toluene Para | 93.15 | 81.79 | 78.89 | 84.74 |
| Meta | 6.85 | 18.21 | 21.11 | 15.26 |
| Ortho | — | — | — | — |

From the above results, it will be seen that para and meta ethyltoluene were exclusively obtained with no production of ortho ethyltoluene.

EXAMPLE 8

A mixture of para and meta ethyltoluene (96% para and 4% meta), essentially free of the ortho isomer, obtained by removal of unreacted toluene and lighter materials from a product, such as described in Example 7, was, without requiring an intermediate distillation to remove the ortho isomer, subjected to dehydrogenation. This was carried out in the presence of steam at 625° C. and a conventional dehydrogenation catalyst containing about 75% $Fe_2O_3$, 20% $K_2O$ and 2% $Cr_2O_3$ at a WHSV (ethyltoluene/steam) of 0.9/2.9 $hr.^{-1}$.

TABLE VII

| Component | Weight Percent |
|---|---|
| Benzene | 0.19 |
| Toluene | 0.80 |
| $C_8$ | 1.12 |
| Styrene | 0.66 |
| Ethyltoluenes | |
| Para | 44.50 |
| Meta | 1.80 |
| Ortho | 0 |
| Vinyltoluenes | |
| Para | 48.96 |
| Meta | 1.97 |
| Ortho | 0 |

Vinyl toluene (99.6% pure) in which the para:meta isomer ratio was 96:4 was isolated from the above product by vacuum distillation.

It is to be noted that if ortho-ethyltoluene had been present to any substantial extent, a difficult distillation, prior to dehydrogenation would have had to be effected due to the proximity of the boiling points of the ethyltoluene isomers, i.e. para 162° C., meta 161.3° C. and ortho 165.1° C.

EXAMPLE 9

Four grams of HZSM-5 having a crystallite size of about 2 microns was pressed into wafers and sized to 14–20 mesh particles. This material was placed in a quartz micro-reactor and treated with steam at 600° C. for seven hours.

The catalyst was then tested for its ability to alkylate ethylbenzene with ethylene to yield diethylbenzene. At a temperature of 400° C. and WHSV (ethylbenzene/ethylene) of 4.29/0.17 $hr.^{-1}$, the ethylbenzene conversion was 27 percent. Seventy (70) percent of the product consisted of diethylbenzene with a para/meta/ortho isomer ratio of 68/32/<0.5.

It will be seen from this ratio that with the use of the steamed crystalline aluminosilicate zeolite catalyst a very enhanced increase in the production of the para isomer and a very substantial decrease in the production of the ortho isomer was achieved.

We claim:

1. Process for the ethylation of a mono alkyl benzene wherein the alkyl substituent contains 1 to 2 carbon atoms to selectively produce the para and meta derivatives of said mono alkyl benzene to the substantial exclusion of the ortho derivative thereof which comprises contacting said mono alkyl benzene under conversion conditions, with ethylene in the presence of a catalyst comprising a crystalline aluminosilicate zeolite, which zeolite is characterized by an activity, in terms of alpha value, of between about 2 and about 5000, a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, said crystalline aluminosilicate zeolite further being characterized by a silica to alumina ratio of at least about 12, and a constraint index within the approximate range of 1 to 12, said catalyst having been subjected to steam treatment at a temperature between about 250° and about 1000° C. for a period of between about 0.5 and about 100 hours.

2. The process of claim 1 wherein said conversion conditions include a temperature between about 250° and about 600° C., a pressure between about 0.1 and about 100 atmospheres utilizing a feed weight hourly space velocity between about 0.1 and about 100 and a molar feed ratio of toluene/ethylene between about 1 and about 10.

3. The process of claim 1 wherein the catalyst is subjected to steam treatment at a temperature between about 400° and about 700° C. for a period of between about 1 and about 24 hours.

4. The process of claim 1 wherein said crystalline aluminosilicate is ZSM-5.

5. The process of claim 1 wherein the steamed catalyst has deposited thereon between about 2 and about 75 weight percent of coke.

6. The process of claim 1 wherein said crystalline aluminosilicate zeolite is admixed with a binder therefor.

7. The process of claim 4 wherein said ZSM-5 is admixed with a binder therefor.

8. The process of claim 1 wherein the crystal size of the crystalline aluminosilicate zeolite is within the approximate range of 0.01 to 0.10 micron.

9. The process of claim 1 wherein the crystal size of the crystalline aluminosilicate zeolite is greater than about 1 micron.

10. The process of claim 1 wherein the crystal size of the crystalline aluminosilicate zeolite is within the approximate range of 1 to 40 microns.

11. The process of claim 1 wherein the crystal size of the crystalline aluminosilicate zeolite is 1 to 6 microns.

12. The process of claim 1 wherein said mono alkyl benzene is toluene.

13. The process of claim 1 wherein said mono alkyl benzene is ethylbenzene.

14. A process for the ethylation of a mono alkyl benzene wherein the alkyl substituent contains 1 or 2 carbon atoms to selectively produce the para and meta derivatives of said mono alkyl benzene to the substantial exclusion of the ortho derivative thereof which comprises contacting said mono alkyl benzene, under conversion conditions, with ethylene in the presence of a catalyst comprising a crystalline aluminosilicate zeolite characterized by a silica to alumina ratio of at least about 12, a constraint index within the approximate range of 1 to 12 and an alkali metal content of less than about 1.5 weight percent, said catalyst having been treated, prior to use, with an atmosphere containing from about 5 to about 100 percent steam at a temperature of from about 250° to about 1000° C for a period of between about 0.5 and about 100 hours.

15. The process of claim 14 wherein said conversion conditions include a temperature between about 250° and about 600° C, a pressure between about 0.1 and about 100 atmospheres utilizing a feed weight hourly space velocity between about 0.1 and about 100 and a molar feed ratio of toluene/ethylene between about 1 and about 10.

16. The process of claim 14 wherein the catalyst is subjected to steam treatment at a temperature between about 400° and about 700° C for a period of between about 1 and about 24 hours.

17. The process of claim 14 wherein said crystalline aluminosilicate is ZSM-5.

18. The process of claim 14 wherein the crystal size of the crystalline aluminosilicate zeolite is greater than about 1 micron.

19. The process of claim 14 wherein said mono alkyl benzene is toluene.

20. The process of claim 14 wherein said mono alkyl benzene is ethylbenzene.

* * * * *

UNITED STATES PATENT AND TRADEMARK OFFICE

CERTIFICATE OF CORRECTION

PATENT NO. : 4,094,921

DATED : June 13, 1978

INVENTOR(S) : W. W. Kaeding and L. B. Young

It is certified that error appears in the above-identified patent and that said Letters Patent are hereby corrected as shown below:

Column 6, line 43, ferrierite patterns exhibit a significant line at "11.38A." should read ferrierite patterns exhibit a significant line at --11.33A.--

Column 7, line 24 quantity of "OH___" is calculated... should read quantity of --$OH^-$-- is calculated...

Column 8, line 56 quantity of "OH___" is calculated... should read quantity of --$OH^-$-- is calculated...

Column 15, line 30 "TAVLE IV" should read --TABLE IV--

Column 17, line 46 ...contains "1 to 2" carbon... should read ...contains --1 or 2--carbon...

Signed and Sealed this

***Twenty-second* Day of *January 1980***

[SEAL]

*Attest:*

SIDNEY A. DIAMOND

*Attesting Officer* *Commissioner of Patents and Trademarks*